(12) United States Patent
Little et al.

(10) Patent No.: US 7,867,168 B2
(45) Date of Patent: Jan. 11, 2011

(54) ULTRASONIC TRANSDUCER HAVING DISTRIBUTED WEIGHT PROPERTIES

(75) Inventors: Blake W. Little, Bothell, WA (US); Lee Dunbar, Bothell, WA (US)

(73) Assignee: SonoSite, Inc., Bothell, WA (US)

( * ) Notice: Subject to any disclaimer, the term of this patent is extended or adjusted under 35 U.S.C. 154(b) by 1093 days.

(21) Appl. No.: 11/599,120

(22) Filed: Nov. 14, 2006

(65) Prior Publication Data

US 2007/0071266 A1   Mar. 29, 2007

Related U.S. Application Data

(63) Continuation-in-part of application No. 10/925,114, filed on Aug. 24, 2004, now abandoned.

(51) Int. Cl.
*A61B 8/14* (2006.01)

(52) U.S. Cl. .............. 600/459; 600/437; 600/443; 600/446; 600/463

(58) Field of Classification Search ............. 600/459, 600/437, 443, 446, 463
See application file for complete search history.

(56) References Cited

U.S. PATENT DOCUMENTS

| | | | |
|---|---|---|---|
| 5,640,960 A * | 6/1997 | Jones et al. | 600/453 |
| 5,772,412 A | 6/1998 | Zytnynski | |
| 5,839,442 A | 11/1998 | Chiang et al. | |
| 5,971,923 A | 10/1999 | Finger | |
| 6,102,863 A | 8/2000 | Pflugrath et al. | |
| 6,113,547 A | 9/2000 | Catallo et al. | |
| 6,120,447 A | 9/2000 | Mullen | |
| 6,142,946 A | 11/2000 | Hwang et al. | |
| 6,238,344 B1 | 5/2001 | Gamelsky et al. | |
| 6,241,673 B1 | 6/2001 | Williams | |
| 6,251,073 B1 | 6/2001 | Imran et al. | |
| 6,416,475 B1 * | 7/2002 | Hwang et al. | 600/441 |
| 6,440,072 B1 | 8/2002 | Schuman et al. | |
| D462,446 S | 9/2002 | Felix et al. | |
| 6,471,651 B1 | 10/2002 | Hwang et al. | |
| 6,475,146 B1 | 11/2002 | Frelburger et al. | |

(Continued)

FOREIGN PATENT DOCUMENTS

WO   WO 00/30540   6/2000

(Continued)

OTHER PUBLICATIONS

European Search Report issued for EP 07250407.9 datedOct. 19, 2007.

(Continued)

*Primary Examiner*—Brian Casler
*Assistant Examiner*—James Kish
(74) *Attorney, Agent, or Firm*—Fulbright & Jaworski L.L.P.

(57) ABSTRACT

Systems and methods which partition ultrasound signal processing between an ultrasound system main processing unit and transducer assembly are shown. A particular division of signal processing functionality disposed in the main processing unit and the transducer assembly may be selected to provide a desired weight balance, a desired level of processing for data communication between the main processing unit and the transducer assembly, etcetera. Battery capacity may additionally or alternatively be partitioned between the main processing unit and the transducer assembly.

15 Claims, 3 Drawing Sheets

U.S. PATENT DOCUMENTS

| | | |
|---|---|---|
| 6,481,887 B1 | 11/2002 | Mirabella |
| D467,002 S | 12/2002 | Felix et al. |
| 6,491,634 B1 | 12/2002 | Leavitt et al. |
| D469,539 S | 1/2003 | Felix et al. |
| D469,877 S | 2/2003 | Felix et al. |
| 6,530,887 B1 | 3/2003 | Gilbert et al. |
| 6,569,102 B2 | 5/2003 | Imran et al. |
| 6,625,252 B2 | 9/2003 | Mirabella |
| 6,936,008 B2 | 8/2005 | Tarakci et al. |
| 6,980,419 B2 | 12/2005 | Smith et al. |
| 2002/0016545 A1 | 2/2002 | Quistgaard et al. |
| 2002/0173721 A1 | 11/2002 | Grunwald et al. |
| 2003/0013959 A1 | 1/2003 | Grunwald et al. |
| 2003/0073894 A1 | 4/2003 | Chiang et al. |
| 2003/0097071 A1 | 5/2003 | Halmann et al. |
| 2003/0139664 A1 | 7/2003 | Hunt et al. |
| 2004/0225220 A1* | 11/2004 | Rich .......................... 600/446 |

FOREIGN PATENT DOCUMENTS

| | | |
|---|---|---|
| WO | WO 00/66001 | 11/2000 |
| WO | WO 2006/023983 | 3/2006 |

OTHER PUBLICATIONS

Examiner's First Report issued for the Australian Application No. 2005-276993, dated Apr. 30, 2009, 2 pages.

International Search Report and the Written Opinion of the International Searching Authority, dated Dec. 21, 2005.

European Search Report issued for Application No. 07250407.9-2305; Dated Sep. 25, 2007; 8 Pages.

* cited by examiner

ULTRASONIC TRANSDUCER HAVING DISTRIBUTED WEIGHT PROPERTIES

CROSS-REFERENCE TO RELATED APPLICATIONS AND PATENTS

The present application is a continuation-in-part of co-pending, commonly assigned, patent application Ser. No. 10/925,114 entitled "Ultrasonic Transducer Having A Thin Wire Interface," filed Aug. 24, 2004, now abandoned the disclosure of which are hereby incorporated herein by reference. The present application is related to co-pending, and commonly-assigned U.S. patent application Ser. No. 10/924,390, entitled "Ultra System Power Management," filed on Aug. 24, 2004; U.S. patent application Ser. No. 10/847,643, filed on May 17, 2004, entitled "Processing Of Medical Signals;" U.S. patent application Ser. No. 10/821,123, filed on Apr. 8, 2004, entitled "Systems And Methods For Providing ASICS For Use In Multiple Applications;" U.S. patent application Ser. No. 10/821,198, filed on Apr. 8, 2004, entitled "System And Method For Enhancing Gray Scale Output On A Color Display;" the disclosures of which are all hereby incorporated.

TECHNICAL FIELD

This disclosure relates to ultrasound devices and more particularly to such devices having a thin wire interface.

BACKGROUND OF THE INVENTION

Ultrasound medical devices are becoming more common. A typical ultrasound device is shown in U.S. Pat. No. 5,772,412 dated Mar. 3, 1998 and U.S. Pat. No. 6,471,651 dated Oct. 29, 2002 which patent is hereby incorporated by reference herein.

A typical implementation of an ultrasound medical device has the transducer portion separate from the main processing unit of the device. Traditionally, the analog and digital signal processing of the raw ultrasound signals to/from a patient are performed in a main processing unit. The raw ultrasound signals are passed to/from the scanhead transducer across a cable to the main processing unit. The cable that connects the ultrasound transducer with the main body of the ultrasound processing unit must be fairly long because the processing unit is not easily moveable and the scanhead must be placed on the anatomy of interest in a variety of positions. The cable is also typically large and heavy because it carries the transmit and receive signals for a number of individual elements of the transducers, located in the transducer head. The length, usually in excess of six feet, coupled with the weight of the cable places significant stress and strain on a sonographer. The cable also adds significant cost and complexity to the system.

Another problem with existing cables is that they typically contain a large number of individual coaxial conductors that are expensive and difficult to connect to a single connector. A connector is often required on the cable since multiple tranducers are used on the system for different applications. The connector, due to the large number of interconnect lines and the sensitive nature of the signals, is therefore large, complicated and expensive. Thus, the overall cable is expensive, troublesome to assemble and repair as well as difficult to use.

The aforementioned large number of individual conductors results from the desire to individually excite the elements of the transducer arrays with electronic wave forms so as to generate mechanical movement of the transducer elements in a controlled fashion and thereby create ultrasound energy which is then transmitted to the patient's body in a desired direction. That is, ultrasound transmit beams may be formed to focus ultrasonic energy at a particular point or region in space and ultrasound receive beams may be formed to collect data along one or more lines or directions to derive information regarding particular structures of interest, such as to form images thereof. The ultrasonic energy is reflected from internal organs (and other items of interest), coming back to the transducer elements where it is converted back to electrical signals for subsequent processing by the processing unit. The signal between the transducer and the processor unit should pass these signals, without significant distortion, attenuation or interference, up and down the connecting cable.

BRIEF SUMMARY OF THE INVENTION

The present invention is directed to systems and methods in which signal processing functionality is partitioned such that a portion of the ultrasound signal processing is contained within the transducer assembly of an ultrasound system, thereby reducing the need for a multiplicity of high performance conductors, or other relatively high bandwidth, high fidelity bandwidth running between the transducer and the main body of the ultrasound system. Embodiments of the present invention are facilitated through the use of a unique architecture to allow for proper power management given the small transducer size and an architecture that exploits the high levels of integration possible on integrated circuit technologies allowing for its implementation in a few highly integrated circuits with virtually no external components outside of the ICs.

In one embodiment, the signal processing functionality disposed within a transducer assembly comprises transmission circuitry, receiver circuitry, and beam formers used to control and generate the beam formed ultrasound signal. Alternative embodiments dispose additional or alternative signal processing functionality within a transducer assembly, depending upon a level of processing desired prior to or after transmission of signals between the transducer assembly and main processing unit. By partitioning the system in this manner the output of the transducer scanhead becomes a digital data stream. All the sensitive analog signals are maintained in close proximity to the transmission/receiver circuitry and transducer elements, thereby eliminating any significant signal degradation allowing increased performance. The digital data stream can also be converted to a serial high-speed bit stream (e.g., using data compression, multiplexing, encoding, etcetera) to further reduce the conductor count and/or bandwidth of a cable or other link carrying signals across the interface between the transducer assembly and main unit. Accordingly, a cable and connector having an extremely low conductor count may be utilized. Also, the signals on the cable are digital and, therefore, the cable does not require as high a fidelity, thereby further reducing the cost and size of the cable and connector.

Embodiments of the invention utilize the foregoing redistribution of signal processing functionality to distribute weight between a transducer assembly and a corresponding main processing unit. Accordingly, a transducer assembly may be provided with a desired amount of mass, such as for an improved user experience, improved interfacing with scanned objects, a more traditional weight, etcetera. Likewise, a main processing unit may be provided with a reduced mass, such as to provide a more portable unit, a better balance of weight between the main processing unit and transducer assembly, etcetera.

A distributed power source configuration may be utilized according to embodiments of the invention such that a portion of the power source is disposed in an ultrasound system main processing unit and another portion of the power source is disposed in the ultrasound system transducer assembly. Such embodiments may be utilized to provide ultra sound systems which do not pass power through a cable or other link connecting the transducer assembly and main processing unit, which provide better balance between the transducer assembly and main processing unit, which provide a transducer assembly having a desired weight, etcetera.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWING

For a more complete understanding of the present invention, reference is now made to the following descriptions taken in conjunction with the accompanying drawing, in which.

DETAILED DESCRIPTION OF THE INVENTION

Figure 1:
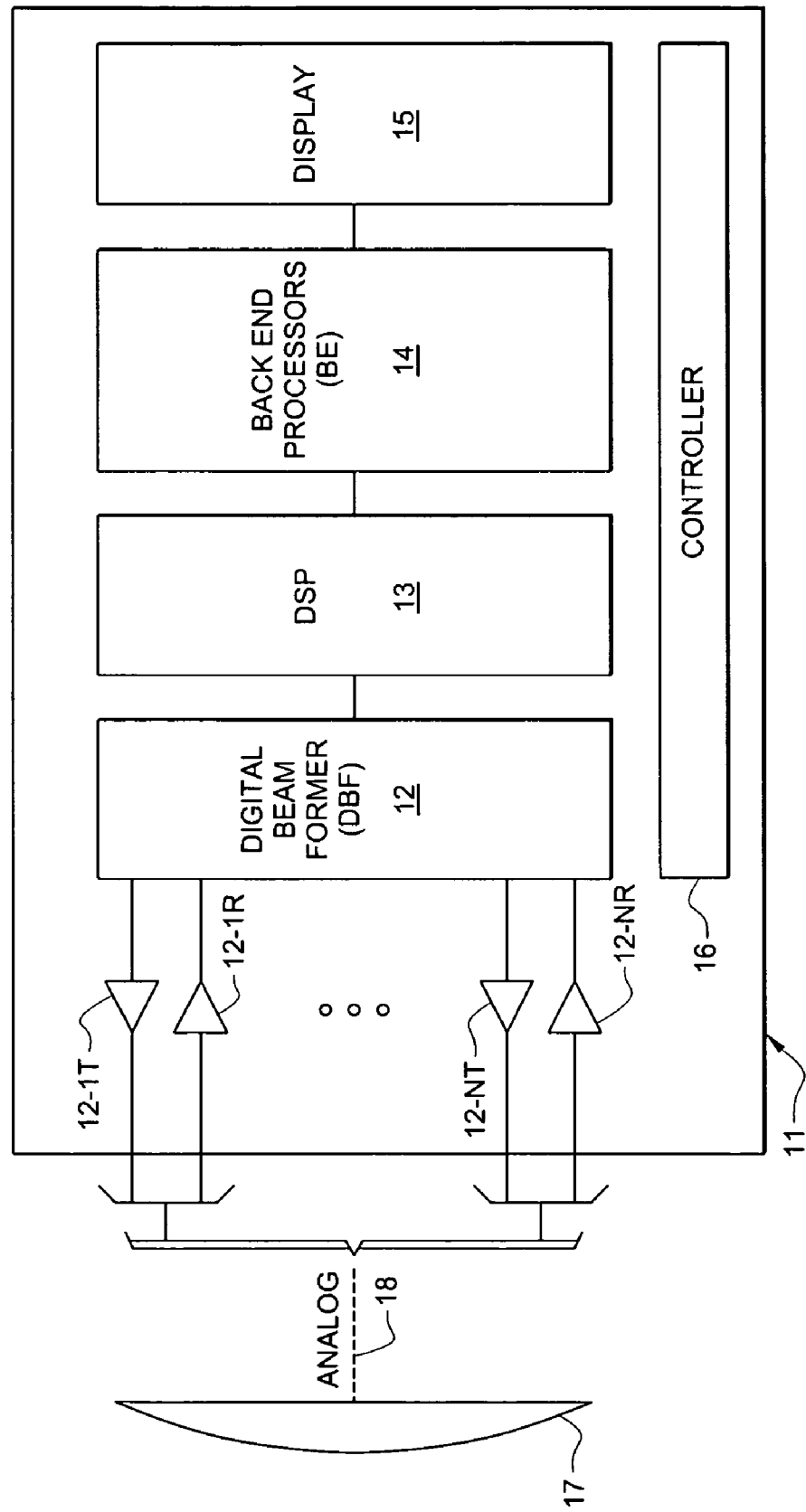
FIG. 1 shows one embodiment of a prior art ultrasound system.

FIG. 1 shows a typical prior art architecture of an ultrasound system as system 10 having transducer array 17, which is coupled via analog cable 18 to individual receiving and transmit channels 12-IT, 12-IR to 12-NT, 12-NR to digital beam former 12. Typically, the Tx and Rx signals are time multiplexed. DSP 13 is comprised of circuits utilized for echo and flow signal processing and includes analytic signal detection and compression, multi-rate filtering, and moving target detection capabilities. Digital signal processor (DSP) 13 provides signals to and receives signals from beam former 12. Back end processing 14 then provides signals to drive display 15 all under control of controller 16. Display 15 provides for display of data including image data. This display could be disposed in main processing unit housing 11, or could be separate from both the main processing unit and from the transducer assembly. The operation of processing elements as set forth above can be as discussed in U.S. Pat. Nos. 5,772,412 and 6,471,651 identified above.

In this arrangement, cable 18 contains a high number (usually on the order of 128 or 256) of individual conductors (typically sets of coaxial conductors) for carrying the analog signals between transducer array 17 and receiving and transmit channels 12-IT, 12-IR to 12-NT, 12-NR. As discussed above, cable 18 is big, bulky, heavy, expensive and not very efficient. The analog signals are also sensitive, often requiring tuning to try to compensate for the loading of the cable.

Figure 2:
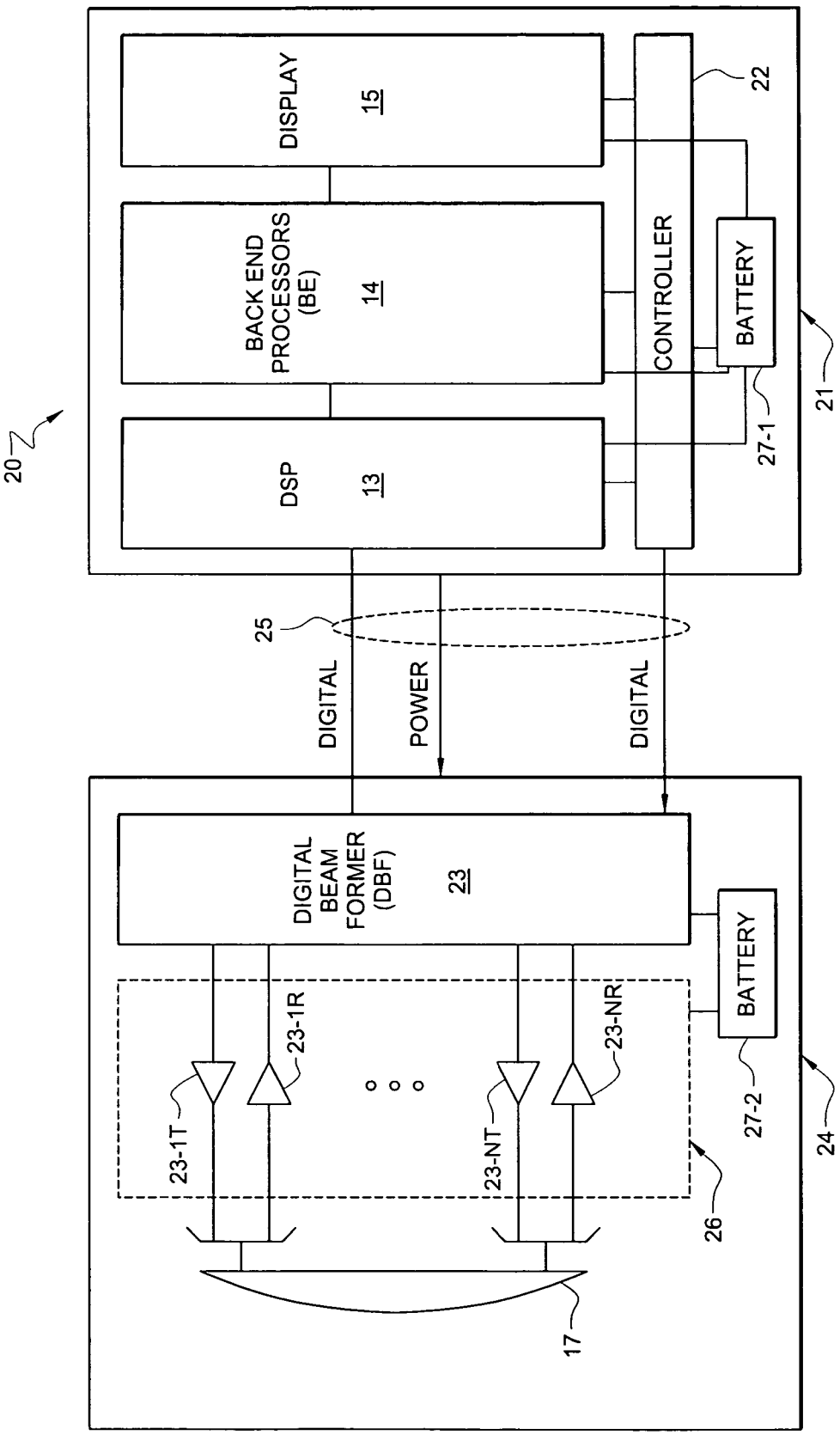
FIG. 2 shows one embodiment of an ultrasound system partitioned to allow for digital signaling between the transducer and the main processor.

FIG. 2 shows one embodiment of ultrasound system 20 in which signal processing functionality is partitioned such that a portion of the ultrasound signal processing is contained within the transducer assembly of an ultrasound system. Although providing similar functional blocks to those described with respect to FIG. 1, the embodiment of FIG. 2 provides a configuration in which miniaturization and integration are leveraged to facilitate a redistribution of the various functional blocks within transducer assembly 24 and main processing unit 21. Accordingly, transmit/receive (Tx/Rx) circuitry 26 of a preferred embodiment comprises pulser circuits, multiplexer circuits, low noise time gain control amplifiers and filters in an application specific integrated circuit (ASIC). Multiple analog to digital (A/D) converters, digital beam forming circuits and control logic are integrated in an ASIC of DBF 23. Embodiments for accomplishing such arrangements are shown in the above-identified application entitled, "Systems And Methods For Providing ASICS For Use In Multiple Applications."

In the embodiment of FIG. 2, the interface between the beam former, such as beam former 23, and subsequent signal processing, such as DSP 13, is moved to transducer assembly 24. Accordingly, beam former 23, transducer array 17, and transmit/receive circuitry 26, such as may comprise amplifiers 23-IT, 23-IR to 23-NT, 23-RT as shown in the illustrated embodiment, used in driving transducer array 17 are disposed in transducer assembly 24 of the illustrated embodiment. This arrangement eliminates analog cable 18 (FIG. 1) replacing it with digital cable 25, running between transducer assembly 24 and processing unit 21, which can be a much smaller cable since only a small number of conductors are needed to provide necessary control and/or signals.

In addition to cable size reduction, this rearrangement of elements also results in a performance gain. By eliminating cable 18, analog loading, distortion and attenuation characteristics are also eliminated allowing for increased performance and signal integrity. Better sensitivity, better response, and better bandwidth are achieved. In addition, this arrangement reduces power loss of the transmitters on the cable.

It should be appreciated that, in addition to providing additional signal processing functionality within transducer assembly 24, embodiments of the invention also provide additional mass within the transducer assembly. As a result of miniaturization and integration advances implemented with respect to medical ultrasound devices developed by SonoSite, Inc., the assignee of the present application, the weight of certain transducer assemblies have been markedly reduced. The present inventors have discovered that, somewhat counter intuitively, transducer assemblies with at least some threshold weight may be preferred by users, such as to give a better feel in operation, to provide a more positive interface with a scanned object, to provide better balance in the hand, etcetera. As the transducer becomes lighter, other design factors become more important, such as the shape, size and cable. These other design factors may influence the minimum acceptable weight. For example, a user may feel the effects of torque, such as may result from a cable connecting the ultrasound and the transducer held by the user hanging down next to the user's hand, with a lighter transducer having a larger cable. According to one embodiment, signal processing circuitry and/or other circuitry is disposed in the transducer assembly, rather than the processing unit assembly, in order to provide a transducer assembly having a desired weight or a weight more typical of historical transducer assemblies while eliminating weight from the processing unit assembly thereby resulting in a lighter, more portable processing unit.

Components which may be distributed or redistributed between a transducer assembly and main processing unit according to embodiments of the invention is not limited to signal processing circuitry. For example, where ultrasound system 20 comprises a portable configuration one or more power sources may be included therein for powering the circuitry thereof. Embodiments of the present invention distribute power sources among the transducer assembly and main processing unit assembly as shown in FIG. 2 to provide a desired weight balance. Energizing a transducer array of an ultrasound system often requires as much as one third of the total power consumed by the system. Accordingly, embodiments of the invention may dispose approximately one third of the power source capacity (e.g., battery 27-2) within transducer assembly 24 and two thirds of the power source capacity (e.g., battery 27-1) within main processing unit assembly 21. Of course, other distribution ratios may be utilized according to embodiments of the invention, if desired. Such distribution of power sources may be further utilized to provide a transducer assembly having a weight more typical of historical transducer assemblies while eliminating weight from the processing unit assembly thereby resulting in a lighter, more portable processing unit.

It should be appreciated that power may continue to be provided through cable 25 in embodiments with distributed power source configurations as described above. For example, a conductor carrying power within cable 25 may be utilized to "trickle" charge battery 27-2 and/or provide power to circuitry of the transducer assembly while the circuitry of transducer assembly 24 is substantially idle, whereas battery 27-2 may be utilized to provide power to circuitry of the transducer assembly when the circuitry of transducer assembly 24 is in a fully operational state. Alternatively, carrying power within cable 25 may be avoided in a distributed power source configuration, such as where transducer assembly 24 is placed in communication with a recharging power source periodically to replenish a power reserve of battery 27-2. For example, a coil (not shown) responsive to radio frequency energy may be disposed within transducer assembly 24 to facilitate wireless recharging of battery 27-2 without the need to dispose any protuberances (e.g., connectors, terminals, etcetera) upon the surface of transducer assembly 24. Alternatively, a recharging interface, such as may comprise one or more connector, terminal, etcetera, may be provided on or in a surface of transducer assembly 24 to facilitate coupling of battery 27-2 to a recharging power supply.

Cable 25 preferably comprises a pair of Low Voltage Differential Signal (LVDS) lines to transmit the digital data back and forth. A USB, USB2, or 1EE1394 type interface, or other standard or proprietary digital interface, could be used between a transducer assembly and processing unit according to embodiments of the invention.

Embodiments of the present invention utilize a wireless interface rather than cable 25. For example, a wireless local area network (WLAN) interface, such as an IEEE 802.11 interface, may be utilized in place of cable 25. Of course, rather than utilizing a standardized wireless interface, embodiments of the present invention may utilize a proprietary wireless interface, if desired. Preferred embodiments of the present invention utilize a standardized wireless interface in order to take advantage of widely available technology and chip sets when implementing the wireless interface. For example, IEEE 802.11 chip sets are readily available wherein a transceiver chip (not shown) may be disposed in transducer assembly 24, coupled to digital beam former 23 at the interfaces shown for cable 25, and a corresponding transceiver chip (not shown) disposed in main processing unit 21, coupled to DSP 13 at the interfaces shown for cable 25. Antennas for such wireless communications may be disposed within the housing assemblies, upon the surfaces thereof, or external thereto.

It should be appreciated that various configurations of ultrasound system 20 may have appreciable transmission bandwidth limitations with respect to the interface between transducer assembly 24 and main processing unit 21. For example, the transmission bandwidths available in many wireless implementations provide bandwidth limitations which are not well suited for transmitting digital data representing beam formed ultrasound signals. However, further signal processing of such signals may reduce the amount of information passed to a next signal processing function. Accordingly, it may be desirable to provide a different distribution of signal processing functionality than that shown in FIG. 2, particularly in certain wireless configurations. For example, it may be desirable to move additional DSP functions to the transducer assembly, thereby further reducing the data bandwidth utilized between the transducer assembly and the main processing unit.

Figure 3:
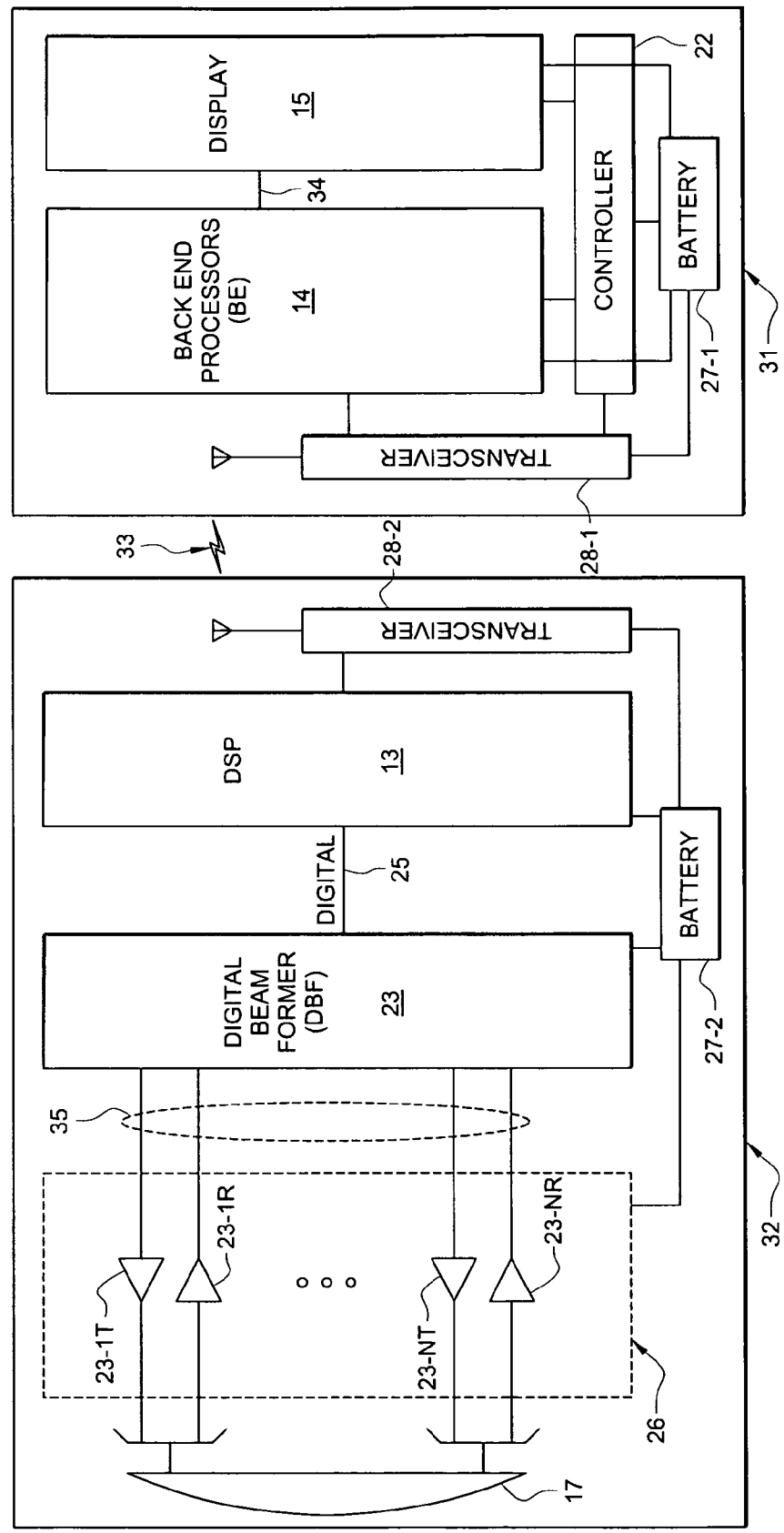
FIG. 3 shows one embodiment for further reducing the data bandwidth between the transducer and the main processor.

FIG. 3 shows an alternative distribution of the representative ultrasound system processing blocks; transmit/receive (Tx/Rx) 26, digital beam former (DBF) 23, digital signal processor (DSP) 13, backend processing (BE) 14 and display 15. Specifically, in the illustrated embodiment of ultrasound system 30 shown in FIG. 3, both DBF 23 and DSP 13 are disposed within transducer assembly 32. Thus further signal processing is provided within the transducer assembly as compared to the configuration illustrated in FIG. 2. As such, less bandwidth may be utilized in passing data between transducer assembly 32 and main processing unit 31. The illustrated embodiment take advantage of this feature to implement a wireless interface, shown as link 33, using transceivers 28-1 and 28-2. Transceivers 28-1 and 28-2 may comprise corresponding radio frequency ASICs or similar chip sets, according to embodiments of the invention.

In a preferred embodiment, DBF 23, DSP 13 and BE 14 would be implemented using digital CMOS ASICS and digital/analog mixed-mode ASICS and Tx/Rx 26 would be implemented based on high-voltage and/or Bi-Cmos technology. The total weight of the scanhead module of one embodiment is less than 20 ounces. Excluding the housing, transducer array 17, in one embodiment, weighs less than 8 ounces. The peak power consumption is approximately 6 watts. Average power consumption with power management is less than 4 watts and the bandwidth of the signals over the interface from the transducer to the processing unit, has been reduced at least on order of magnitude from approximately 400 Mbps to under 40 Mbps. In one embodiment, for a video display having 128×512 pixels, a data rate of 16 Mbps is possible using the concepts discussed herein.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A system comprising:
   an ultrasound transducer assembly including an ultrasound transducer array and signal processing circuitry coupled to said transducer array operable to process analog signals from said transducer array and provide digital information there from;
   a main processing unit separate from said ultrasound transducer assembly and in communication therewith operable to receive said digital information from said ultrasound transducer assembly; and
   a digital data cable coupled between said ultrasound transducer assembly and said main processing unit carrying said digital information there between;
   wherein said system is powered by a battery power source, wherein portions of the battery power source are distributed between the ultrasound transducer assembly and the main processing unit.

2. The system of claim 1, wherein said distribution of said battery source is configured at least in part to result in a desired total weight of said ultrasound transducer assembly, wherein said desired total minimum weight is configured to counterbalance torque forces felt by a user of said transducer assembly.

3. The system of claim 1, wherein an amount of said processing circuitry included in said ultrasound transducer assembly is configured at least in part to result in a desired total weight of said ultrasound transducer assembly.

4. The system of claim 1, wherein said processing circuitry comprises a digital beam former coupled to said transducer array.

5. The system of claim 4, wherein said processing circuitry comprises a digital signal processor coupled to said digital beam former.

6. The system of claim 1, wherein said digital cable is configured to convey power from said main processing unit to said ultrasound transducer assembly for charging a battery therein.

7. The system of claim 1, wherein an amount of said processing circuitry included in said ultrasound transducer assembly is configured at least in part to facilitate a wireless communication link between said ultrasonic transducer assembly and said main processing unit.

8. The system of claim 1, wherein said ultrasound transducer assembly further includes a first radio frequency transceiver and said main processing unit includes a wireless transceiver, and wherein said digital information is carried between said ultrasound transducer assembly and said main processing unit using said first and second wireless transceivers.

9. The system of claim 8, wherein said first and second wireless transceivers comprise radio frequency transceivers.

10. The system of claim 8, wherein said first and second wireless transceivers provide communication of said digital information using a standardized wireless communication protocol.

11. The system of claim 10, wherein said standardized wireless communication protocol is selected from the group consisting of a wireless local area network protocol and a wireless personal area network protocol.

12. A method comprising:
    providing an ultrasound transducer assembly having a transducer array and signal processing circuitry coupled to said transducer array;
    providing a main processing unit having signal processing circuitry in communication with said signal processing circuitry of said ultrasound transducer assembly via digital data communication wherein said ultrasound transducer assembly is connected to said main processing unit with a digital data cable configured to carry said digital information there between; and
    distributing battery capacity between said ultrasound transducer assembly and said main processing unit to provide a desired distribution of weight between said ultrasound transducer assembly and said main processing unit.

13. The method of claim 12, further comprising:
    distributing signal processing circuitry between said signal processing circuitry of said ultrasound transducer assembly and said signal processing circuitry of said main processing unit to provide a desired distribution of weight between said ultrasound transducer assembly and said main processing unit.

14. The method of claim 12, wherein said digital data communication is provided by a wireless connection.

15. The method of claim 12 wherein said desired total distribution of weight is configured to provide sufficient weight to said transducer assembly to counterbalance torque forces felt by a user of said transducer assembly.

* * * * *